(12) United States Patent
Chen et al.

(10) Patent No.: US 8,283,464 B2
(45) Date of Patent: Oct. 9, 2012

(54) PROCESS FOR SYNTHESIZING AND PURIFYING SUCRALOSE

(75) Inventors: Xinmin Chen, Shanghai (CN); Yanbing Bai, Hangzhou (CN); Jianxin Peng, Shanghai (CN)

(73) Assignees: Zhejiang Hangzhou Xinfu Pharmaceutical, Co., Ltd., Hangzhou (CN); Shanghai Tongchen Biotech, Co., Ltd., Shanghai (CN)

( * ) Notice: Subject to any disclaimer, the term of this patent is extended or adjusted under 35 U.S.C. 154(b) by 143 days.

(21) Appl. No.: 12/747,379

(22) PCT Filed: Dec. 19, 2008

(86) PCT No.: PCT/CN2008/002036
§ 371 (c)(1),
(2), (4) Date: Jul. 26, 2010

(87) PCT Pub. No.: WO2009/089684
PCT Pub. Date: Jul. 23, 2009

(65) Prior Publication Data
US 2010/0292462 A1    Nov. 18, 2010

(30) Foreign Application Priority Data
Dec. 19, 2007 (CN) .......................... 2007 1 0172558

(51) Int. Cl.
*C13K 5/00* (2006.01)
*C13K 7/00* (2006.01)
*C07H 1/00* (2006.01)
*C07H 3/00* (2006.01)
*C08B 37/00* (2006.01)

(52) U.S. Cl. .................................. 536/123.13; 536/124
(58) Field of Classification Search ........................ None
See application file for complete search history.

(56) References Cited

U.S. PATENT DOCUMENTS

| 4,675,393 A | * | 6/1987 | Coxon ........................ 536/18.6 |
| 4,783,526 A | * | 11/1988 | O'Brien et al. .............. 536/18.5 |
| 4,950,746 A | * | 8/1990 | Navia ............................ 536/119 |
| 5,498,709 A | * | 3/1996 | Navia et al. ................... 536/124 |

FOREIGN PATENT DOCUMENTS

| CN | 101012250 A | 8/2007 |
| CN | 101029062 A | 9/2007 |
| CN | 101245085 A | 8/2008 |

OTHER PUBLICATIONS

Robyt, Essentials of Carbohydrate Chemistry, Springer, 1998, p. 77.*

* cited by examiner

*Primary Examiner* — Layla Bland
(74) *Attorney, Agent, or Firm* — Chainey P. Singleton; Edwin S. Flores; Chalker Flores, LLP

(57) ABSTRACT

The present invention discloses a process for synthesizing sucralose, which comprises reacting sucrose with acetic anhydride in the solvent of a N-amide compound in the presence of an organic complex alkali metal salt catalyst to produce sucrose-6-acetate, and then chlorinating and deacetylating the sucrose-6-acetate to give sucralose. The present invention also discloses a process for purifying sucralose, which comprises purifying crude sucralose with one or more organic solvents to obtain purified sucralose.

14 Claims, No Drawings

PROCESS FOR SYNTHESIZING AND PURIFYING SUCRALOSE

TECHNICAL FIELD

The present invention relates to the field of chemical synthesis technique. Specifically, the present invention relates to a process for synthesizing and purifying sucralose.

BACKGROUND ART

Sucralose,
Chemical name: 4,1',6'-trichloro-4,1',6'-trideoxygalactosucrose;
English name: 4,1',6'-tricholorgalacosucrose (sucralose);
Structural formula:

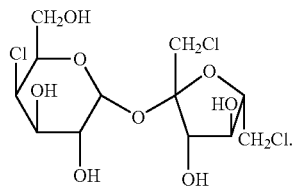

Sucralose, which is a novel non-nutrition sweetener with high sweetness that is as 600 times as that of sucrose, becomes the ideal sweet substitute for the diabetes patients and has been permitted by more than twenty countries to be used as a food sweetener, because it does not participate in metabolism, is not absorbed by human body, is not utilized by the dental caries bacteria, or does not cause dental caries.

At the beginning, sucralose was successfully prepared by Tate & Lyle Company, UK in 1975 by using chemical synthesis. This chemical synthesis method mainly includes monogroup protected synthesis and hologroup protected synthesis, both of which use sucrose as a raw material.

Monogroup protected methods, such as the acetate method reported in U.S. Pat. Nos. 4,889,928 and 5,449,772 and the dibutyltin oxide method reported in U.S. Pat. Nos. 5,023,329 and 4,950,746, use the sixth site hydroxyl group that is more active in sucrose molecule. The hydroxyl group on the sixth site is protected selectively by acetyl group or benzoyl group to prepare sucrose-6-acetate or sucrose-6-benzoylester, then the sucrose-6-acetate or sucrose-6-benzoylester is chlorinated selectively by VILSMERIER agent to obtain trichlorosucralose-6-acetate (benzoylester), and finally the sucralose is obtained after hydrolysis.

Hologroup protected methods, such as the method reported in U.S. Pat. Nos. 4,783,526; 4,801,700; 4.343.934; and 4,362,869, use the difference in the steric hindrance amongst the eight hydroxyl groups in the sucrose molecule, which is to say, use one group with larger volume to selectively protect the to primary hydroxyl group with a smaller steric hindrance, then the remaining hydroxyl groups are totally acetylated, and then the protecting group is removed under acidic conditions. The acetyl group on the fourth site is transferred onto the sixth site so that the three chlorinated sites meet certain requirements. Then three hydroxyl groups are chlorinated, and the sucralose is obtained by hydrolysis and deacetylating.

CN03126655.X discloses a method for synthesizing sucralose, characterized in that sucrose as a raw material is subjected to transesterification with ethyl acetate in a solution of N,N-dimethylformamide and in the presence of a sulfate solid acid catalyst or a sulfate solid acid catalyst adsorbed on the macromolecular carriers to produce sucrose-6-acetate, which is subjected to chlorination and alcoholysis to give sucralose.

CN03805527.9 discloses a novel extracting method for purifying sucralose.

CN200610034731.3 discloses a method for preparing sucralose, comprising firstly preparing sucrose-6-ester in a separate-type electrolyzer device using indirect electrooxidation synthesis technique, and then chlorinating and hydrolyzing sucrose-6-ester to produce sucralose.

CN200710037102.0 discloses a method for preparing sucralose, comprising reacting sucrose with an acetylating agent in the presence of a polymer loaded organotin catalyst to produce sucrose-6-ester with high chemical purity, and then chlorinating and alkali hydrolyzing sucrose-6-ester to produce sucralose.

Among these synthesis methods, the hologroup protected methods including too much procedures, are relatively complicated and quite high in cost; whilst the monogroup protected methods for synthesizing sucrose-6-acetate are low in chemical yield, and are difficult and complex to purify the water phase of the product, and are not desirable in the purity of product. For the dibutyltin oxide method, since the dibutyltin oxide used as a catalyst is not able to recycle, the production cost is high and the product is not suitable for application due to the presence of tin-based impurities.

SUMMARY OF THE INVENTION

The present invention is aimed to address the disadvantages of the prior arts by providing a novel method for preparing sucralose. The advantages of the instant method are simple process, easy to handle, high in chemical yield and purity of product, and low in production cost.

The method for preparing sucralose in accordance with the instant invention includes synthesizing process and purifying process. In first aspect of the invention, the process for synthesizing sucralose is characterized in that sucrose as a raw material is reacted with acetic anhydride in a solvent of N-amide compounds and in the presence of an organic complex alkali metal salt catalyst to produce sucrose-6-acetate with high purity and yield, and the sucrose-6-acetate is chlorinated to give tricholorosucrose-6-acetate, which is finally deacetylated and purified in an anhydrous solvent to produce sucralose. The finished product thus obtained has a higher chemical yield and purity.

The N-amide compounds are N,N-dimethylformamide (DMF), N,N-diethylformamide, N,N-dipropylformamide, N,N-dimethylacetamide, or mixtures thereof. Preferably, N,N-dimethylformamide (DMF) is used as the reaction solvent of the instant invention due to its solubility and safety to sucrose.

In a preferred embodiment of the present invention, sucrose is dissolved in the solvent of cyclohexane and DMF, the resultant is refluxed to dehydrate in the presence of an organic complex alkali metal salt catalyst and then cooled to an appropriate temperature, and an acetylating agent acetic anhydride is added dropwise. After reacting for 2 to 8 hours, the product is washed with water to remove the solvent, and then sucrose-6-acetate is obtained.

The said organic complex alkali metal salt catalyst includes one or a mixture of more of the following components:
①Alkali metal salts, such as sodium acetate, potassium acetate, sodium carbonate, potassium carbonate, and the like, preferably sodium acetate.

②Organic compounds, such as pyridine, diethylamine, triethylamine, DMAP (4-dimethylaminopyridine), aromatic acid, aromatic sulfonic acid, and the like, preferably DAMP (4-dimethylaminopyridine).

③Natural organic substances, such as theophylline, aminophylline, nicotine extracts, and the like, preferably nicotine extracts.

The said organic complex alkali metal salt catalyst is preferably a complex of sodium acetate and DMAP with a weight ratio of sodium acetate:DMAP being 0-100:100-50.

The more preferable weight ratio is sodium acetate:DMAP of 10-30:90-70.

The molar ratio of the raw materials is sucrose:catalyst: acetic anhydride of 1:0.01-0.5:1.1-2.

Trichlorosucrose-6-acetate is synthesized by dissolving sucrose-6-acetate in DMF solvent, then adding dropwise into the prepared Vilsmeier reagent synthesized from thionyl chloride and DMF, and chlorinating at −20-120° C. for 5-15 hours, and subsequently neutralizing, filtrating, extracting with ethyl acetate, decoloring the reactant and recycling the solvent to give trichlorosucrose-6-acetate.

The molar ratio of the raw materials is sucrose-6-acetate: thionyl chloride of 1:5-20.

The deacetylation reaction of trichlorosucrose-6-acetate includes the steps of dissolving trichlorosucrose-6-acetate in anhydrous methanol, ethanol or propanol, adding a deacetylating agent, and carrying out deacetylation reaction at 0-50° C.

The said deacetylating agent is preferably ethylenediamine, tert-butylamine, tert-pentylamine, and the like, and more preferably tert-butylamine. The molar ratios of the raw materials are such that trichlorosucrose-6-acetate:methanol is 1:5-20 and trichlorosucrose-6-acetate:deacetylating agent is 1:0.001-0.1.

In second aspect of the present invention, the process for purifying sucralose comprises the steps of directly purifying trichlorosucrose-6-acetate with one or more than two anhydrous organic solvents after deacetylation to give the finished product of sucralose.

The organic solvents are any one of alcohols, ethers, ketones, esters, or a mixture of any combination thereof.

The alcohols are selected from any one of methanol, ethanol, propanol, ethylene glycol, glycerin, isopropanol, isobutyl alcohol, or a mixture of any combination thereof.

The ethers are selected from any one of ethyl ether, dimethyl ether, isopropyl ether, methyl tert-butyl ether, or a mixture of any combination thereof.

The ketones are selected from any one of acetone, methyl isopropyl ketone, butanone, methyl isobutyl ketone, or a mixture of any combination thereof.

The esters are selected from any one of ethyl formate, isopropyl formate, isobutyl acetate, butyl acetate, tert-butyl acetate, propyl acetate, isopropyl acetate, pentyl acetate, isopentyl acetate, methyl formate, hexyl acetate or a mixture of any combination thereof.

The solvent is preferably selected from any one of methanol, ethanol, isopropanol, isobutyl alcohol, ethyl formate, isobutyl acetate, butyl acetate, tert-butyl acetate, propyl acetate, isopropyl acetate, pentyl acetate, isopentyl acetate, methyl formate, isopropyl formate, hexyl acetate, acetone, butanone, isopropyl ether, or a mixture of any combination thereof.

The advantageous effects of the present invention are as follows:

The method for preparing sucralose in accordance with the present invention can attain a chemical yield of up to more than 50% and a product content of up to 99-102% by weight on the basis of sucrose, both of which meet the standard of FCC V.

Compared to the prior synthesis methods, the method of the present invention has the advantages of simple process, mild reaction conditions, extremely high conversion rate and purity of product, lower cost and very high applicability to industrial production.

Compared to the current crystallization purification process, the process for purifying sucralose in accordance with the present invention avoids the complicated repeated crystallization, the reduction in yield and the waste of solvent. Therefore, the purifying process of this invention is more adaptable and easier to operate, compared to the existing crystallization purification process.

BEST MODE FOR CARRYING OUT THE INVENTION

The present invention will be further illustrated with reference to the following examples. It should be appreciated that these examples are for illustrative purpose only and not intended to limit the scope of the invention.

Example 1

Synthesis of Sucrose-6-Acetate 100 g sucrose, 350 ml N,N-dimethylformamide, 100 ml cyclohexane and 2 g catalyst (the weight ratio of sodium acetate:DMAP=0.5:1.5) are added into a 1000 ml four-necked flask, heated to reflux, and dehydrated for 3 hours under stirring, then cooled down to 25° C. 40 g acetic anhydride is added dropwise, and the temperature is kept for 5 hours for reaction, and then the catalyst is filtrated and recovered. The mother liquor is placed under reduced pressure to recover DMF, and finally 108 g syrup is obtained. The content of sucrose-6-acetate in the syrup is 90.2% by weight, which is measured by HPLC (provided with differential detector), and the yield is 90.8%.

Synthesis of Trichlorosucrose-6-Acetate 108 g syrup mentioned as above is dissolved in 500 ml N,N-dimethylformamide to reserve. 500 ml N,N-dimethylformamide is added into a 2000 ml four-necked flask, and cooled down to −10° C., then 300 ml thionyl chloride is so added dropwise under the control of dropping speed that the temperature during the whole dropping process is maintained below −10° C. After completion of dropping, the resultant solution is stirred at −10° C. for 30 minutes, then the well-dissolved solution of sucrose-6-acetate in DMF is slowly added dropwise. After completion of dropping, the temperature of thus prepared solution is increased to 70-80° C. for 5 hours for reaction, then the temperature is increased to 115° C. and kept at 115° C. for 4 hours for reaction. The reactant solution is cooled down to a temperature of 0-5° C., and 30% aqueous sodium hydroxide solution is added dropwise under stirring for neutralization until pH value of 7. The resultant reactant is filtrated to remove salts, and the mother liquor is concentrated under reduced pressure to dryness, then the resultant is dissolved by adding 300 ml water and extracted with 400 ml×3 ethyl acetate for three times. The ethyl acetate layers are combined and decolored with activated carbon, and then ethyl acetate is recovered. After recrystallization with water and solvent twice, 50 g trichlorosucrose-6-acetate is obtained, the content of which is 99% by weight as measured by HPLC.

Synthesis and Purification of Sucralose 50 g trichlorosucrose-6-acetate and 500 ml anhydrous methanol are added at the same time into a 1000 ml three-necked flask. After being heated to dissolve, 4 ml tert-butylamine is added and the pH value of the reactant solution is adjusted to 8-9. The reactants are allowed to react at room temperature for 5 hours. After completion of the reaction, the solution is neutralized with a weak acidic resin to a pH value of 7. After decoloring and filtrating, methanol is vapored out under vacuum. 450 ml isopropyl formate is then added. After purifying, recovering solvent, cooling down for crystallizing and filtrating, recrystallizing with ethyl formate and drying under vacuum, about 37.6 g sucralose product with a purity of 99% is obtained, and the product yield is 79.9%.

Example 2

Synthesis of Sucrose-6-Acetate 100 g sucrose, 350 ml N,N-dimethylformamide, 100 ml cyclohexane and 2 g catalyst (the weight ratio of sodium acetate:DMAP=50:50) are added into a 1000 ml four-necked flask, heated to reflux, and dehydrated for 3 hours under stirring, then cooled down to 25° C. 40 g acetic anhydride is added dropwise, and the temperature is kept for 5 hours for reaction, and then the catalyst is filtrated and recovered. The mother liquor is placed under reduced pressure to recover DMF, and finally 104 g syrup is obtained. The content of sucrose-6-acetate in the syrup is 90.8% by weight, which is measured by HPLC (provided with differential detector), and the yield is 88%.

The procedures for synthesizing trichlorosucrose-6-acetate and the procedures for synthesizing and purifying sucralose are the same as those of EXAMPLE 1. Finally, 33 g sucralose product with a purity of 99.1% is obtained.

Example 3

Synthesis of Sucrose-6-Acetate 100 g sucrose, 350 ml N,N-dimethylformamide, 100 ml cyclohexane and 2 g catalyst (the weight ratio of sodium acetate:DMAP=100:75) are added into a 1000 ml four-necked flask, heated to reflux, and dehydrated for 3 hours under stirring, then cooled down to 25° C. 40 g acetic anhydride is added dropwise, and the temperature is kept for 5 hours for reaction, and then the catalyst is filtrated and recovered. The mother liquor is placed under reduced pressure to recover DMF, and finally 106 g syrup is obtained. The content of sucrose-6-acetate in the syrup is 88.6% by weight, which is measured by HPLC (provided with differential detector), and the yield is 87.86%.

The procedures for synthesizing trichlorosucrose-6-acetate and the procedures for synthesizing and purifying sucralose are the same as those of EXAMPLE 1. Finally, 30 g sucralose product with a purity of 99.01% is obtained.

Example 4

Synthesis of Sucrose-6-Acetate 100 g sucrose, 350 ml N,N-dimethylformamide, 100 ml cyclohexane and 2 g catalyst (the weight ratio of sodium acetate:DMAP=75:60) are added into a 1000 ml four-necked flask, heated to reflux, and dehydrated for 3 hours under stirring, then cooled down to 25° C. 40 g acetic anhydride is added dropwise, and the temperature is kept for 5 hours for reaction, and then the catalyst is filtrated and recovered. The mother liquor is placed under reduced pressure to recover DMF, and finally 108 g syrup is obtained. The content of sucrose-6-acetate in the syrup is 89.4% by weight, which is measured by HPLC (provided with differential detector), and the yield is 90.06%.

The procedures for synthesizing trichlorosucrose-6-acetate and the procedures for synthesizing and purifying sucralose are the same as those of EXAMPLE 1. Finally, 33 g sucralose product with a purity of 99.02% is obtained.

Comparative Example 1

Synthesis of Sucrose-6-Acetate 100 g sucrose, 350 ml N,N-dimethylformamide, 100 ml cyclohexane and 2 g catalyst (p-toluene sulphonic acid) are added into a 1000 ml four-necked flask, heated to reflux, and dehydrated for 3 hours under stirring, then cooled down to 25° C. 40 g acetic anhydride is added dropwise, and the temperature is kept for 5 hours for reaction. The mother liquor is placed under reduced pressure to recover DMF, and finally 115 g syrup is obtained. The content of sucrose-6-acetate in the syrup is 78.4% by weight, which is measured by HPLC (provided with differential detector), and the yield is 84.1%.

The procedures for synthesizing trichlorosucrose-6-acetate and the procedures for synthesizing and purifying sucralose are the same as those of EXAMPLE 1. Finally, 27 g sucralose product with a purity of 98% is obtained.

Comparative Example 2

Synthesis of Sucrose-6-Acetate 100 g sucrose, 350 ml N,N-dimethylformamide, 100 ml cyclohexane and 2 g catalyst (sulfuric acid) are added into a 1000 ml four-necked flask, heated to reflux, and dehydrated for 3 hours under stirring, then cooled down to 25° C. 40 g acetic anhydride is added dropwise, and the temperature is kept for 5 hours for reaction. The mother liquor is placed under reduced pressure to recover DMF, and finally 102 g syrup is obtained. The content of sucrose-6-acetate in the syrup is 65.4% by weight, which is measured by HPLC (provided with differential detector), and the yield is 62.2%.

The procedures for synthesizing trichlorosucrose-6-acetate and the procedures for synthesizing and purifying sucralose are the same as those of EXAMPLE 1. Finally, 12 g sucralose product with a purity of 98.1% is obtained.

Comparative Example 3

Synthesis of Sucrose-6-Acetate 100 g sucrose, 350 ml N,N-dimethylformamide, 100 ml cyclohexane and 2 g catalyst (ferric sulfate solid acid) are added into a 1000 ml four-necked flask, heated to reflux, and dehydrated for 3 hours under stirring, then cooled down to 25° C. 40 g acetic anhydride is added dropwise, and the temperature is kept for 5 hours for reaction. The mother liquor is placed under reduced pressure to recover DMF, and finally 115 g syrup is obtained. The content of sucrose-6-acetate in the syrup is 80.4% by weight, which is measured by HPLC (provided with differential detector), and the yield is 86.25%.

The procedures for synthesizing trichlorosucrose-6-acetate and the procedures for synthesizing and purifying sucralose are the same as those of EXAMPLE 1. Finally, 28 g sucralose product with a purity of 99.01% is obtained.

Example 5

The procedures for synthesizing sucrose-6-acetate and the procedures for synthesizing trichlorosucrose-6-acetate are the same as those of EXAMPLE 1, and sucralose is synthesized by the following procedures:

50 g trichlorosucrose-6-acetate and 500 ml anhydrous methanol are added at the same time into a 1000 ml three-necked flask. After being heated to dissolve, 4 ml triethylamine is added and the pH value of the reactant solution is adjusted to 8-9. The reactant is allowed to react at room temperature for 5 hours. After completion of the reaction, the solution is neutralized with a weak acidic resin to a pH value of 7. After decoloring and filtrating, methanol is vapored out under vacuum. 450 ml isopropyl formate is then added. After purifying, recovering solvent, cooling down for crystallizing and filtrating, recrystallizing with ethyl formate and drying under vacuum, about 30 g sucralose product with a purity of 99.1% is obtained.

Examples 6-12

The procedures for synthesizing sucrose-6-acetate and the procedures for synthesizing trichlorosucrose-6-acetate are the same as those of EXAMPLE 1, and sucralose is synthesized by the following procedure:

50 g trichlorosucrose-6-acetate and 500 ml anhydrous methanol are added at the same time into a 1000 ml three-necked flask. After being heated to dissolve, 4 ml tert-butylamine is added and the pH value of the reactant solution is adjusted to 8-9. The reactant is allowed to react at room temperature for 5 hours. After completion of the reaction, the solution is neutralized with a weak acidic resin to a pH value of 7. After decoloring and filtrating, methanol is vapored out under vacuum to obtain the crude sucralose. The crude sucralose is purified with one or more organic solvent, and then subjected to crystallization purification by use of the solubility differences between sucralose and its impurities in different solvents, and then dried under vacuum to give the sucralose product.

Compared to the current crystallization purification process, the process for purifying sucralose in accordance with the present invention avoids the complicated repeated crystallization, the reduction in yield and the waste of solvent. Therefore, the purifying process of this invention is more adaptable and easier to operate, compared to the existing crystallization purification process.

Example 6

50 g trichlorosucrose-6-acetate and 500 ml anhydrous methanol are added at the same time into a 1000 ml three-necked flask. After being heated to dissolve, 4 ml tert-butylamine is added and the pH value of the reactant solution is adjusted to 8-9. The reactant is allowed to react at room temperature for 5 hours. After completion of the reaction, the solution is neutralized with a weak acidic resin to a pH value of 7. After decoloring and filtrating, methanol is vapored out under vacuum till dryness to obtain the crude sucralose. 100 ml methanol is then added to dissolve the solid sucralose while stirring in a water bath of 30-35° C. The solvent methanol is recovered under a vacuum of −0.098 MPa, and the solution is concentrated to 70 ml and cooled down to 10° C. for crystallizing for 3 hours. After filtrating and drying under vacuum, 37.8 g sucralose product with a purity of 99.2% by weight is obtained, and the yield of sucralose product is 80%.

Example 7

To the crude sucralose obtained through the procedure described in EXAMPLE 6, 100 ml anhydrous ethanol is added to dissolve the solid sucralose while stirring in a water bath of 30-35° C. The solvent ethanol is reovered under a vacuum of −0.098 MPa in a water bath of 40-45° C., and the solution is concentrated to 70 ml and cooled down to 10° C. for crystallizing for 3 hours. After filtrating and drying under vacuum, 37.2 g sucralose product with a purity of 99.1% by weight is obtained, and the yield of sucralose product is 78.68%.

Example 8

To the crude sucralose obtained through the procedure described in EXAMPLE 6, 100 ml acetone is added to dissolve the solid sucralose while stirring in a water bath of 30-35° C. The solvent acetone is recovered under a vacuum of −0.098 MPa, and the solution is concentrated to 70 ml and cooled down to 10° C. for crystallizing for 3 hours. After filtrating and drying under vacuum, 37 g sucralose product with a purity of 99.0% by weight is obtained, and the yield of sucralose product is 78.25%.

Example 9

To the crude sucralose obtained through the procedure described in EXAMPLE 6, 100 ml dimethyl ether is added to dissolve the solid sucralose while stirring in a water bath of 40-45° C. The solvent dimethyl ether is recovered under a vacuum of −0.098 MPa, and the solution is concentrated to 70 ml and cooled down to 10° C. for crystallizing for 3 hours. After filtrating and drying under vacuum, 36 g sucralose product with a purity of 99.1% by weight is obtained, and the yield of sucralose product is 76.12%.

Example 10

To the crude sucralose obtained through the procedure described in EXAMPLE 6, 100 ml ethyl acetate is added to dissolve the solid sucralose while stirring in a water bath of 50-55° C. The solvent ethyl acetate is recovered under a vacuum of −0.098 MPa in a water bath of 40-45, and the solution is concentrated to 70 ml and cooled down to 10° C. for crystallizing for 3 hours. After filtrating and drying under vacuum, 37.6 g sucralose product with a purity of 99.0% by weight is obtained, and the yield of sucralose product is 79.5%.

Example 11

To the crude sucralose obtained through the procedure described in EXAMPLE 6, 50 ml anhydrous methanol, 50 ml butyl acetate and 50 ml ethyl acetate are added to dissolve the solid sucralose while stirring in a water bath of 40-45° C. The solvent comprising methanol, butyl acetate and ethyl acetate is recovered under a vacuum of −0.098 MPa in a water bath of 30-35° C., and the solution is concentrated till crystallization begins and cooled down to 10° C. for crystallizing for 3 hours. After filtrating and drying under vacuum, 37.5 g sucralose product with a purity of 99.1% by weight is obtained, and the yield of sucralose product is 79.31%.

Example 12

To the crude sucralose obtained through the procedure described in EXAMPLE 6, 50 ml anhydrous methanol, 50 ml acetone 50 ml ethyl acetate and 50 ml butyl acetate are added to dissolve the solid sucralose while stirring in a water bath of 30-35° C. The solvent comprising methanol, acetone, ethyl acetate and butyl acetate is recovered under a vacuum of −0.098 MPa in a water bath of 30-35° C., and the solution is concentrated till crystallization begins and cooled down to 10° C. for crystallizing for 3 hours. After filtrating and drying under vacuum, 37.5 g sucralose product with a purity of 99.0% by weight is obtained, and the yield of sucralose product is 79.3%.

The scope of the present invention is not limited by the embodiments, and the embodiments are just intended to be the individual examples for illustrating each aspect of the invention. The functionally equivalent methods and components are within the scope of the invention. In fact, besides the disclosure of the invention, many kinds of modifications can be easily realized by the skilled persons in the art with reference to the description hereinabove. The modifications are also within the scope of the appended claims. Each of the references mentioned as above is herein incorporated by reference in its entirety.

The invention claimed is:

1. A process for synthesizing sucralose, characterized by reacting sucrose as a raw material with acetic anhydride in the solvent of a N-amide compound in the presence of an organic complex alkali metal salt catalyst to produce sucrose-6-acetate, and chlorinating and deacetylating the sucrose-6-acetate to give sucralose;
   wherein the organic complex alkali metal salt catalyst is a mixture of an alkali metal salt and an organic compound, wherein the alkali metal salt is selected from the group consisting of sodium acetate, potassium acetate, sodium carbonate, potassium carbonate, and a combination thereof, and the organic compound is selected from the group consisting of pyridine, diethylamine, triethylamine, DMAP, an aromatic acid, an aromatic sulfonic acid, theophylline, aminophylline, and a mixture thereof.

2. The process according to claim 1, wherein the N-amide compound is selected from the group consisting of N,N-dimethylformamide, N,N-diethylformamide, N,N-dipropylformamide, N,N-dimethylacetamide, and a mixture thereof.

3. The process according to claim 1, wherein the N-amide compound is N,N-dimethylformamide.

4. The process according to claim 1, wherein the alkali metal salt is sodium acetate.

5. The process according to claim 1, wherein the organic compound is DMAP.

6. The process according to claim 1, wherein the organic complex alkali metal salt catalyst is a complex of sodium acetate and DMAP with a weight ratio of sodium acetate:DMAP=10-100:100-50.

7. The process according to claim 1, wherein the organic complex alkali metal salt catalyst is a complex of sodium acetate and DMAP with a weight ratio of sodium acetate:DMAP=10-30:90-70.

8. The process according to claim 1, wherein, in the procedure of preparing sucrose-6-acetate, the molar ratio of the raw materials sucrose:organic complex alkali metal salt catalyst:acetic anhydride=1:0.01-0.5:1.1-2.

9. The process according to claim 1, wherein the procedure of preparing trichlorosucrose-6-acetate comprises the steps of dissolving the sucrose-6-acetate in DMF solvent, adding dropwise into the prepared Vilsmeier reagent synthesized from thionyl chloride and DMF, carrying out chlorination reaction at −20-120° C. for 5-15 hours, and subsequently neutralizing, filtrating, extracting with ethyl acetate, decoloring and recovering the solvent to give trichlorosucrose-6-acetate.

10. The process according to claim 9, wherein, in the procedure of preparing trichlorosucralose-6-acetate, the molar ratio of the raw materials sucrose-6-acetate:thionyl chloride=1:5-20.

11. The process according to claim 1, wherein the deacetylation reaction of trichlorosucralose-6-acetate comprises the steps of dissolving the trichlorosucralose-6-acetate in methanol, ethanol, propanol or a mixture thereof, then adding a deacetylating agent, and carrying out the deacetylation reaction at 0-50° C.

12. The process according to claim 11, wherein the deacetylating agent is selected from the group consisting of ethylenediamine, tert-butylamine, tert-pentylamine or a mixture thereof.

13. The process according to claim 12, wherein the deacetylating agent is tert-butylamine.

14. The process according to claim 1, wherein, in the procedure of trichlorosucralose-6-acetate deacetylation reaction, the molar ratios of:
   trichlorosucralose-6-acetate:methanol=1:5-20, and
      trichlorosucralose-6-acetate:the deacetylating agent=1:0.001-0.1.

* * * * *